United States Patent
Keil et al.

(10) Patent No.: US 8,415,633 B2
(45) Date of Patent: Apr. 9, 2013

(54) METHOD AND DEVICE FOR MONITORING THE INTENSITY OF AN ELECTRON BEAM

(75) Inventors: Gernot Keil, Braunweiler (DE); Alois Monzel, Mörstadt (DE)

(73) Assignee: KHS GmbH, Dortmund (DE)

( * ) Notice: Subject to any disclaimer, the term of this patent is extended or adjusted under 35 U.S.C. 154(b) by 0 days.

(21) Appl. No.: 13/133,749

(22) PCT Filed: Apr. 20, 2010

(86) PCT No.: PCT/EP2010/002396
§ 371 (c)(1),
(2), (4) Date: Jun. 9, 2011

(87) PCT Pub. No.: WO2010/121775
PCT Pub. Date: Oct. 28, 2010

(65) Prior Publication Data
US 2011/0233414 A1 Sep. 29, 2011

(30) Foreign Application Priority Data
Apr. 21, 2009 (DE) .......................... 10 2009 018 210

(51) Int. Cl.
*G01T 1/24* (2006.01)
(52) U.S. Cl. .................................... 250/370.01
(58) Field of Classification Search ............... 250/252.1, 250/461.1, 459.1
See application file for complete search history.

(56) References Cited

U.S. PATENT DOCUMENTS

| | | | |
|---|---|---|---|
| 2,717,964 A | 9/1955 | Lawrence et al. | |
| 4,349,808 A | 9/1982 | Kraus | |
| 4,658,136 A | 4/1987 | Ohtaka et al. | |
| 5,483,072 A * | 1/1996 | Coe .......................... | 250/385.1 |
| 5,783,828 A | 7/1998 | Pacenti et al. | |
| 6,657,212 B2 | 12/2003 | Komori et al. | |
| 7,375,345 B2 | 5/2008 | Kristiansson et al. | |
| 2004/0113084 A1 | 6/2004 | Nakata et al. | |
| 2004/0227095 A1* | 11/2004 | Gerstenmayer et al. ... | 250/370.1 |
| 2008/0073549 A1 | 3/2008 | Avnery | |
| 2010/0054987 A1 | 3/2010 | Krueger et al. | |

FOREIGN PATENT DOCUMENTS

| | | |
|---|---|---|
| DE | 1122739 | 1/1962 |
| DE | 2920901 | 11/1980 |
| DE | 4108768 | 9/1992 |
| DE | 69621382 | 10/2002 |
| DE | 60017689 | 12/2005 |
| DE | 102008045187 | 3/2010 |
| EP | 0583974 | 2/1994 |
| JP | 2005024307 | 1/2005 |
| WO | 01/14911 | 3/2001 |

OTHER PUBLICATIONS

Nablo et al., "REal time monitoring of electron processors," 1995, Radiation Physics and Chemistry, vol. 46, No. 4-6, pp. 1377-1383.*

(Continued)

*Primary Examiner* — Kiho Kim
(74) *Attorney, Agent, or Firm* — Occhiuti Rohlicek & Tsao LLP

(57) ABSTRACT

The method and the device are used to monitor the intensity of an electron beam. In order to detect changes in intensity of the electron beam, electromagnetic radiation directly or indirectly emitted by the electron beam is detected and evaluated. This particularly refers to the evaluation of ultraviolet radiation and/or radiation in the range of visible light.

22 Claims, 2 Drawing Sheets

OTHER PUBLICATIONS

Figure 1:
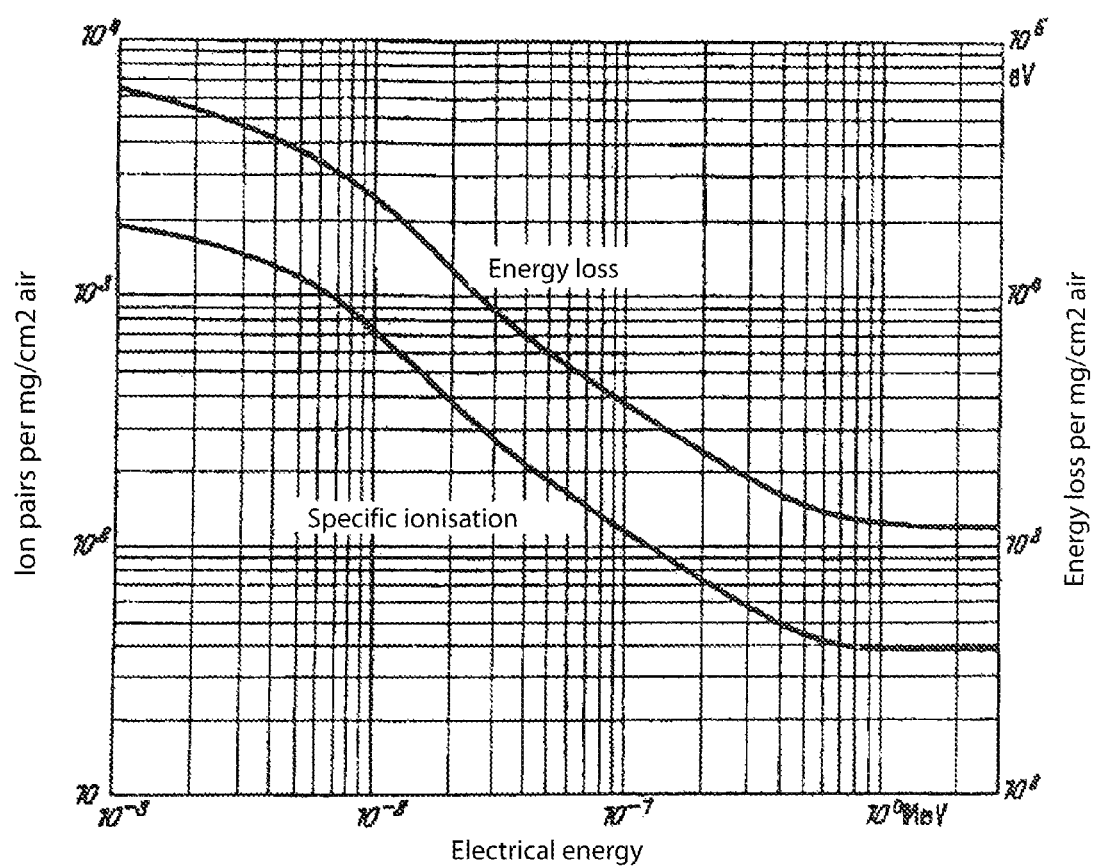

Kneeland, D.R., et al. "Industrial use of the real time monitor for quality assurance in electron processing" *Radiation Physics and Chemistry*. vol. 55, No. 4 (Jul. 11, 1999) pp. 430-431.

Bohne, W., et al. "Beam-Current measurement based on residual gas ionization" *Nuclear Instruments & Methods in Physics Research*. vol. 113, No. 1 (Jun. 1, 1996) pp. 78-80.

Reich, B.G. "Dosimetrie ionisierender Strahlung" Teubner, Stuttgart (1990) p. 69.

Kuchling, H. "Taschenbuch der Physik", Carl Hanser Verlag, 16th Edition (1999) p. 572.

Knoll, Glenn F. "Radiation Detection and Measurement" $3^{rd}$ Edition (1999) pp. xi-xiv.

* cited by examiner

METHOD AND DEVICE FOR MONITORING THE INTENSITY OF AN ELECTRON BEAM

CROSS-REFERENCE TO RELATED APPLICATIONS

This application is the National Stage of International Application No. PCT/EP2010/002396, filed on Apr. 20, 2010, which claims the priority of German Patent Application No. 10 2009 018 210.1, filed on Apr. 21, 2009. The contents of both applications are hereby incorporated by reference in their entirety.

The invention relates to a method for monitoring the intensity of an electron beam.

The invention also relates to a device for monitoring the intensity of an electron beam.

Such electron beams can be generated for example in tubular devices which are configured similarly to X-ray tubes and within which a glowing metallic emission element is disposed. In this respect the electrons are generated by thermionic emission and are accelerated inside the tube to high kinetic energies. The correspondingly accelerated electrons leave the tubular device through an exit window at the end of the acceleration section. Typically the exit window is thinly and/or narrowly configured and electrically connected to ground potential. Such devices are also known as electron guns.

After leaving the exit window the electrons enter the atmospheric environment where they propagate. A maximum propagation distance is given by the kinetic energy of the electrons.

According to a typical embodiment, an electron current is generated which exhibits an intensity in the range of 100 µA (microampere) to 200 mA (milliampere). A continuous operation of the tubes is also typically provided to achieve a constant emission rate of electrons. A constant acceleration voltage is also typically used to generate an electron current that does not vary over time.

Because of the design of the tubes which are used however, small voltage dips occur from time to time which can be caused for example by sparks along the surface of ceramic insulators. Such voltage dips act electrically like a brief short-circuit and cause a decrease in the kinetic energy of the electrons in the electron stream, with possibly an attendant drop in the beam's intensity and/or the range of the electrons.

It is also not possible to absolutely rule out the occurrence of a brief total failure of the electron beam as a result of such influences. Depending on the particular causes, such a failure can last for a period ranging from a few microseconds to several milliseconds. Downtimes which last for more than around 1 millisecond can be detected by monitoring the voltage and current characteristic of the power supply unit that supplies the tube. Shorter downtimes however are not, or at least not reliably, detected because of time constants in the filtering of the power supply unit and because of realised sampling rates of the monitoring of the voltage and current characteristic.

An application of such electron beams can be used for example to sterilise the surface of a packing material. In an application of this type, the surface of the packing material is completely swept by the electron beam by a suitable deflection of the electron beam and/or by moving the packing material relative to the electron source, at least in specified regions, in order to perform reliable sterilisation. Consequently in the event of dips in intensity of the electron beam, a brief loss of the electron beam or an energy dip of the electron beam, in the absence of appropriate countermeasures the performance of the sterilisation operation will be incomplete, which is unacceptable.

It proves to be technically extremely difficult to reliably avoid the intensity dips, energy dips and/or brief failures of the electron beam while maintaining economical boundary conditions. Efforts are therefore being made to detect corresponding intensity fluctuations quickly and reliably in order to influence the deflection of the electron beam or the path of the executed movements in such a way that every portion of the surface of the packing material to be sterilised is exposed to a sufficiently intensive electron beam for a sufficient length of time.

Within the scope of the present invention, the term packing material must be construed to mean any material that is suitable for wrapping or receiving perishable goods. This relates both to flexible materials such as films as well as rigid materials such as, for example, cans made from sheet metal or bottles or jars made from glass and semi-rigid materials such as, for example, plastic bottles, plastic cups etc.

The object of the present invention is to provide a method of the type indicated at the outset such that reliable intensity monitoring can be carried out.

This object is inventively solved in that, to detect changes in the intensity of the electron beam, an electron radiation or electromagnetic radiation directly or indirectly generated by the electron beam is detected and evaluated.

As used within the scope of the present invention, the words "a radiation or electromagnetic radiation directly or indirectly generated by the electron beam" are to be construed to mean that the object of the invention relates to the detection of (electromagnetic) radiations that can occur in different ways. On the one hand this relates to an electron radiation which is generated directly by the electron beam in that for example an electron is detached from the envelope of an atom or molecule and directly strikes the radiation-sensitive component which is used for the detection. This electron radiation can be detected using for example temperature-sensitive resistors such as PT100, PTC, NTC of the type known to a person skilled in the art. Preferential use in this regard is made of components which react very rapidly to temperature changes and which can therefore detect the very least change in the electron radiation.

On the other hand it concerns electromagnetic radiation which is only indirectly generated by the electron beam, for example by the recombinations—described in greater detail below—of electron-ion pairs and the electromagnetic radiations produced as a result.

A further object of the present invention is to design a device of the type described at the outset so as to provide rapid and reliable intensity monitoring.

This object is inventively solved in that a detector is provided for the measurement of an electromagnetic radiation generated directly or indirectly by the electron beam, and in that the detector is connected to an evaluator for detecting changes in the intensity of the generated electromagnetic radiation.

Figure 2:
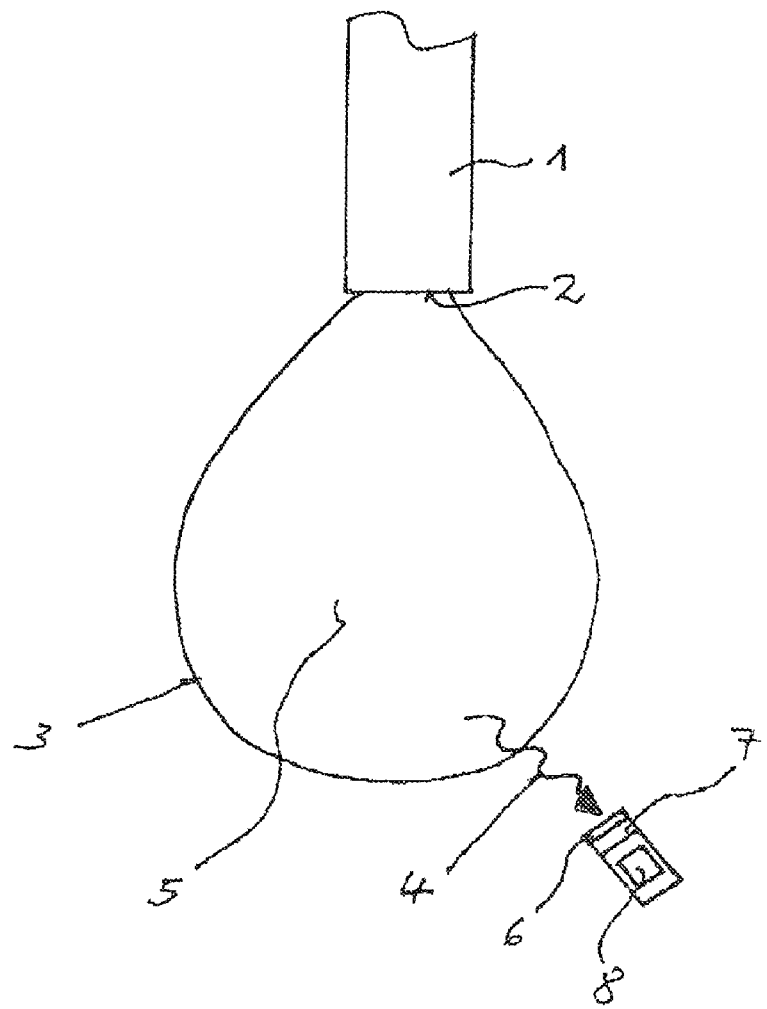

The present invention is described hereinbelow by reference to an exemplary embodiment. Specifically, FIG. 1 shows in a diagram the conditions of the energy loss of electrons as they pass through air, as known to a person skilled in the art, and FIG. 2 shows an inventive device in a simplified representation.

A measurement device for monitoring the electromagnetic radiation emitted by the electron beam can be realised with small spatial dimensions and inexpensively. A corresponding detector which detects the radiation of the plasma generated by the electron beam has a very low error such that measurement times or observation times of just fractions of milliseconds (time constants) are sufficient for signal filtering, i.e. for detecting a change in the electron beam.

The detector can be positioned outside the electron beam such that its thermal load is low, which has an extremely positive effect on the service life of such a detector.

The intensity of the emitted electromagnetic radiation directly correlates with the intensity of the electron beam, and the measuring of the electromagnetic radiation can be carried out with extremely good absolute accuracy.

A measurement in a characteristic frequency range is effected by evaluating an ultraviolet radiation.

It is also proposed for a light radiation to be evaluated.

A particularly simple constructional technical implementation is assisted by the electromagnetic radiation being evaluated during a propagation of the electron beam within atmospheric air.

According to a preferred application, it is proposed for the electron beam to be used for bacterial reduction in the region of the surface of a packing material.

It is particularly proposed for the bacterial count in the region of the surface of a container to be reduced.

A compact design is assisted by the electromagnetic radiation being detected by a semiconductor sensor.

The use of a light-sensitive diode, also referred to as a photodiode, as semiconductor sensor contributes to an economical implementation.

In a further version of the embodiment, a CCD chip, a light-sensitive CMOS chip or a phototransistor is used as semiconductor sensor. A version of the embodiment that uses a light-sensitive resistor is also conceivable.

FIG. 1 plots typical characteristics of a specific ionisation and of an energy loss against electron energy. The curve labelled specific ionisation indicates the number of ion pairs formed by an electron with an energy of 1 keV to 3 MeV during irradiation of a column of air of 1 $mg/cm^2$. The term single ion pair is used in this context to mean a group of one electron and one ion, this being referred to hereinbelow as electron-ion pair.

The curve labelled energy loss describes the energy loss of electrons in air when irradiating a column of air with a mass per unit area of 1 $mg/cm^2$. Effects which occur during the interaction of electrons with matter are usually expressed in terms of mass per unit area because—irrespective of the type of matter, i.e. irrespective of the so-called absorber material—the same masses per unit area of different absorbers produce roughly the same effects. Thus roughly the same energy loss $\Delta E$ of the electron beam when irradiating a column of argon or a column of nitrogen of the same mass per unit area a is to be expected as when irradiating a column of air of the same mass per unit area.

The number of electron-ion pairs that is generated also roughly follows this rule. "Roughly" in this context should be construed as meaning that the anticipated dependencies can vary by only ±15% material-specifically for absorber compositions with atomic numbers Z between 6 and 20. For all other absorbers, the variations between the individual materials are greater. The effects of the energy loss of electrons in absorbers are described by the Bethe-Bloch equation which is explained in "Dosimetrie ionisierender Strahlung", Reich B. G. Teubner, Stuttgart 1990, p. 69.

A preferred application for the inventive method and the inventive device is effected in conjunction with the monitoring of the intensity of an electron beam which is used for the sterilisation of packing material surfaces. For such irradiation purposes, electrons are accelerated inside a tube for generating the electron beam in such a way that an electron energy in the range of 60 keV to 2 MeV is realised. The electron radiation leaves the tube in the region of an exit window and enters an atmospheric environment or an environment which consists of a foreign gas such as for example argon or nitrogen and could replace the atmospheric environment in order to obtain oxygen-freedom in the region of the packing material.

In the region of the exit window the energy of the electrons is reduced, with the extent of this reduction being dependent on the thickness of the exit window, on the material of the exit window and on the kinetic energy of the electrons.

After they pass through the exit window the electrons suffer a further permanent energy loss as they pass through the atmospheric environment. This energy loss is caused primarily by pulse transmission, wherein the exiting electrons generate electron-ion pairs, excited ions, excited molecules, molecule fragments and radicals, for example. Overall, the exiting electrons generate a plasma in the atmospheric environment. The region in which the electron beam of the electron gun is retarded can also generally be filled by gases other than air, for example by argon, nitrogen, helium or such like. This applies equally to the following descriptions.

FIG. 1 shows by way of example the generation rate of electron-ion pairs as specific ionisation. It also shows the energy loss of electrons in an energy range of between 1 keV and 3 MeV for an absorption train of 1 $mg/cm^2$ air which is equivalent to a column of air of approx. 8.3 mm at a temperature of 293 Kelvin and a pressure of 1013.25 mbar. The corresponding energy losses result in an electron beam of for example 130 keV in atmospheric air exhibiting a propagation distance of some 20 cm. Consequently packing material surfaces that are more than 20 cm distant from the exit window are not reached by an electron beam having this energy.

To resolve the object of the present invention, the present invention makes use of the effect that at least a significant part of the original kinetic energy of the electrons is consumed in that the electrons which propagate out from the exit window transmit their kinetic energy through impulses to the atmosphere which they penetrate. In the process, as the electrons propagate and impact against the particles of the atmosphere that surrounds them, electrons are permanently knocked out of the envelopes of the atoms or molecules of the said particles as a result of which pairs of free electrons and ions are again created. Thus the electron beam continuously generates a plasma as its propagates.

From the specialist literature, for example H. Kuchling, "Taschenbuch der Physik", Carl Hanser Verlag, 16th Edition, page 572, it is known that the mean ionisation constant for air is 33.85 eV, so it is possible to calculate, for a known energy loss of an electron in generating an electron-ion pair in an absorber, the total number of pairs formed by an electron of the electron beam along its path.

In the case of an electron leaving the exit window with an energy of 130 keV, this electron according to FIG. 1 will attain an energy loss of 3.3 keV at least for the initial path of 8.3 mm in the absorber. Consequently 97 electron-ion pairs are generated through the impacts that produce this energy loss. For all other paths that are traveled in the absorber, the number of generated electron-ion pairs increases because the energy loss rises as electron energy falls. The use of a value of 100 generated electron-ion pairs in an absorber path of 8.3 mm for the following estimate can therefore be regarded as conservative.

That the electron beam can be detected and its intensity monitored with the required precision is shown by the following calculation example:

An electron with an energy of 130 keV generates:

24 mg/cm²·100 electron-ion pairs per(1 mg/cm²)= 2400 electron-ion pairs.

Beam currents within a range of 100 µA to 200 mA for example are used to sterilise packing materials with electron beams that propagate through air.

The following calculation example relates to a beam current of 1 mA with which good to very goods results are achieved in the sterilisation of packing materials.

A current of 1 mA corresponds to a number of $6.25 \cdot 10^{15}$ electrons per second. Therefore a beam current of 1 mA generates at least $6.25 \cdot 10^{15} \cdot 2400$ electron-ion pairs per second from air, or $1.5 \cdot 10^{19}$ electron-ion pairs per second.

Almost all of these electron-ion pairs recombine immediately, with a large part of the energy that is released during recombination being emitted in the form of radiation in the range of UV light or visible light, 'light radiation' for short.

The exact proportion of the quanta of light radiation to quanta of other ranges or to radiationless transitions cannot be stated, however the proportion—as is generally known to the person skilled in the art—is closer to 50% than to 1%.

A proportion of the recombination in the range of light radiation can therefore be regarded as an extremely conservative estimate. Of the $1.5 \cdot 10^{19}$ electron-ion pairs per second therefore, at least $1.5 \cdot 10^{17}$ photons in the range of light radiation are emitted.

Starting from the exit window of the electron beam, the UV or light radiation takes place from a balloon-shaped region, the balloon-shaped region being defined by the range of the electron radiation and the multiple scattering of the electrons. The light radiation propagates isotropically in space.

Only a very small area element of the balloon-shaped region needs be monitored to fulfil the object of the present invention. For example, the monitoring of an area element of a size of approx. 0.2 cm², equivalent to a circular monitoring window with a diameter of 5 mm, is sufficient.

If we assume a detector with a sensitive area of 0.2 cm² (5 mm diameter) and which sits at a distance of 30 cm from the centre of the recombination region and sights on the centre, then because of the ratio of both solid angles, viz. of the full solid angle of $\pi r^2$ in which the light radiation is emitted and wherein r is the distance of the centre of the recombination region from the location of the detector, and because of the solid angle occupied by the detector area relative to the centre of the radiation emission volume, the detector only sees the 57600-th part of the $1.5 \cdot 10^{17}$ photons that are emitted per second as light radiation.

Light-sensitive diodes are available for a very wide sensitivity range which already begins at a wavelength of some 200 nm and goes beyond the visible range. The response probability of such radiation-sensitive chips or components (light-sensitive diodes, radiation-sensitive diodes, CCD chips, CMOS chips, photodiodes, phototransistors, photoresistors) is typically considerably greater than 50%, i.e. at least every 2nd quantum is also detected, as a result of which the detector in this example detects $1.3 \cdot 10^{12}$ light quanta per second.

A meaningful check of the electron current requires a control signal with an accuracy of around 0.001 with a sampling rate of $10^4$ per second. This means that we need an electron current monitor which compares an actual value with the nominal value every 100 µs, where the actual value should have an accuracy of 1% o.

Because the light quanta are emitted statistically and in high numbers, viz. $1.3 \cdot 10^8$ light quanta per 100 µs which are then transformed into a current, the error ΔI of the current signal I can be easily calculated.

It is generally known from mathematics that the accuracy ΔI of statistically occurring events—in the case in point therefore the accuracy of the measured and/or calculated value for the strength of the electron beam—is equal to the 'root of events' over the 'total number of events', with the equation:

$$\Delta I = \frac{\sqrt{n}}{n}$$

where n=number of events

This is why, with such a high number of events (number of events=$1.3 \cdot 10^8$) a relative error of the current signal of $8.8 \cdot 10^{-5}$ is achieved for sampling rates of 100 µs. This figure counts as excellent and is probably attained by no other detection method.

The estimate described presupposes that the monitoring region is free from any daylight so that the signal to be monitored is not sitting on a high background signal. To this end, the region to be monitored must be embodied so that no foreign light, i.e. for example daylight or light from light fittings, could have a disturbing effect in it.

A further embodiment of the detector uses an optic which restricts the measurable solid angle region and which may also screen off any existing stray radiation of daylight.

Owing to the restriction of the detector's field of vision, this may reduce the number of incident light quanta on the sensitive diode, but even with a photon flow of only $1.3 \cdot 10^6$ quanta falling on the detector per 100 µs interval, the achieved statistical accuracy would still be of the order of $8.8 \cdot 10^{-4}$.

In a further technical embodiment of the detector, a colour filter which allows a small spectral range to pass to the detector is connected upstream of the detector. In this way the spectral range can be restricted so that only characteristic emission lines of the plasma are allowed to pass into the detector for current conversion. This embodiment is particularly interesting when the region in which the electron beam treats the packing material is flooded with a pure gas. The treated region is flooded with nitrogen or argon for example to prevent the packing material from being altered by the oxygen present in the air.

For another variant of this exemplary embodiment it is proposed to configure the colour filter in such a way that one is only sensitive to emission lines of the nitrogen or of the argon in order to monitor the intensity of the electron beam.

For a further variant of this exemplary embodiment it is proposed to configure the colour filter in such a way that one is only sensitive to the emission lines of oxygen in order to monitor the ingress of oxygen into the treated region.

The detector may moreover be combined with an electronic circuit, for example a circuit for monitoring the electron beam or electron current, wherein preferentially the strength of the electron current can be captured.

In this case it is particularly beneficial if the electronic circuit makes it possible to specify one or a plurality of preferably arbitrarily selectable limits or switching points such that certain actions are initiated when the actual strength of the electron current reaches, falls below or exceeds these switching points.

For example, a first switching point that is linked to the signal 'electron current dipped' can be provided. The signal 'electron current dipped' can also only be output when the electron current is undershot for a certain time.

A second switching point may also be provided, this second switching point being higher than the first switching point. The second switching point is compared with the first switching point such that the signal 'electron current dipped' is output only when the second switching point is not exceeded again after a certain selectable time.

A detector for the measurement of this radiation can be embodied for example with an area of around 0.2 cm². This corresponds to a diameter of around 5 mm in the case of a circular detector area. A typical distance from the centre of the recombination region and hence from the centreline of the electron beam is around 30 cm. Sensors with other cross-sections may of course also be used and other distances from the recombination region may be selected.

A typical embodiment of a detector of this kind is effected in the form of light-sensitive semiconductor diodes. Such diodes have a sensitivity range that extends over a wavelength range from around 200 nm up to the range of visible light. It is also possible to use CCD chips as detectors.

According to a preferred constructional implementation the detector is disposed in such a way that, in the main at least, only the electromagnetic radiation emitted by the electron beam is captured. To this end the sensor is shielded so that only an at most insignificant quantity of daylight or light from lighting fittings can enter the range of the detector.

According to another embodiment of the present invention, the detector can also be disposed so that it looks at the plasma through the wall of a transparent or translucent packing material. For example the electron beam can be used to stabilise or disinfect the inner packing material surface of a PET bottle or other hollow-body-shaped packing material and can generate the disinfection plasma or sterilisation plasma that is necessary for this in the hollow body of the packing material. In this regard the detector is advantageously disposed in such a way that it is aimed through the wall at the plasma generated in the hollow body and so monitors the radiation emission of the plasma present in the hollow body. With this embodiment too, the detector can be equipped with an optic and/or a colour filter.

The packing material can have the form of plastic or of glass, for example, or may also consist of another material, in which case it is necessary for the packing material to be transparent, permeable or translucent for the radiation that is produced during the recombination of the electron-ion pairs—at least for parts of said radiation.

A further embodiment of the present invention employs the effect that not all electron-ion pairs recombine immediately after their generation, and/or that in the course of this process, electrons take a different direction than the original direction of the electron beam with the result that these electrons can be detected without the electron beam itself having to be detected. As already described hereinbefore, these electrons too can be detected by suitable components, thereby again making it possible to configure an extremely advantageous device for monitoring the intensity of an electron beam.

| Reference list: | |
|---|---|
| 1 | Electron emitter |
| 2 | Exit window |
| 3 | Boundary of the balloon-shaped region of UV radiation or light radiation |
| 4 | Light quantum or UV quantum |
| 5 | Balloon-shaped region of UV radiation or light radiation |
| 6 | Filter |
| 7 | Optics |
| 8 | Light-sensitive element |

The invention claimed is:

1. A method for monitoring an intensity of an electron beam that generates a plasma during propagation thereof, said method comprising detecting and evaluating electron radiation or electromagnetic radiation that is directly or indirectly generated by the electron beam in order to detect changes in the intensity of the electron beam, wherein detecting and evaluating comprises providing a detector designed for metrological registration of said electron radiation or electromagnetic radiation, and causing said detector to inspect said plasma through a transparent or translucent packing material.

2. The method of claim 1, wherein detecting and evaluating electron radiation or electromagnetic radiation comprises evaluating electromagnetic ultraviolet radiation.

3. The method of claim 1, wherein detecting and evaluating electron radiation or electromagnetic radiation comprises evaluating the radiation during propagation of the electron beam through a propagation medium selected from the group consisting of atmospheric air, nitrogen, and argon.

4. The method of claim 1, further comprising using the electron beam for bacterial reduction in a region of a surface of a packing material.

5. The method of claim 1, further comprising using the electron beam to reduce bacterial count in a region of the surface of a container.

6. The method of claim 1, further comprising detecting, with a semiconductor sensor, the radiation generated by the electron beam.

7. The method of claim 6, wherein detecting the radiation comprises detecting the radiation with a semiconductor sensor that includes a radiation-sensitive or light-sensitive diode.

8. The method of claim 6, further comprising selecting the semiconductor sensor to include at least one of a CCD chip, a CMOS chip, a photodiode, a phototransistor, and a photoresistor.

9. The method of claim 6, further comprising causing the radiation generated by the electron beam, on its way to the semiconductor sensor, to be restricted in spectral range so that only characteristic emission lines of the plasma pass to the detector.

10. The method of claim 6, wherein detecting, with a semiconductor sensor, the radiation generated by the electron beam comprises receiving, at the semiconductor sensor, radiation that occurs in an interior of a hollow body.

11. The method of claim 1, wherein detecting and evaluating electron radiation or electromagnetic radiation comprises evaluating electromagnetic light radiation.

12. An apparatus for monitoring intensity of an electron beam that generates a plasma during propagation thereof, said apparatus comprising: a detector designed for metrological registration of electron radiation or electromagnetic radiation generated directly or indirectly by said electron beam, said detector being disposed to look at said plasma through walls of a transparent or translucent packing material, and an evaluator connected to the detector for detecting changes in intensity of the electron radiation or electromagnetic radiation generated by the electron beam.

13. The apparatus of claim 12, wherein the detector is configured to capture electromagnetic ultraviolet radiation.

14. The apparatus of claim 12, wherein the detector is disposed along a propagation path of the electron beam, said propagation path extending through ambient air.

15. The apparatus of claim 12, wherein the detector is disposed along a propagation path of the electron beam, said propagation path running a gas medium consisting of a gas selected from the group consisting of nitrogen and argon.

16. The apparatus of claim 12, wherein the detector is configured as part of a device for bacterial reduction in a region of a surface of a packing material.

17. The apparatus of claim 12, wherein the detector is configured as part of a device for bacterial reduction in a region of a surface of a container.

18. The apparatus of claim 12, wherein the detector comprises a semiconductor sensor.

19. The apparatus of claim 18, wherein the semiconductor sensor comprises a radiation-sensitive diode or a light-sensitive diode.

20. The apparatus of claim 18, wherein the semiconductor sensor comprises at least one of a CCD chip, a CMOS chip, a photodiode, a phototransistor, and a photoresistor.

21. The apparatus of claim 18, wherein the semiconductor sensor is disposed to receive electromagnetic radiation occurring inside a packing material body.

22. The apparatus of claim 12, wherein the detector is configured to capture electromagnetic light radiation.

* * * * *